United States Patent [19]
Honold et al.

[11] Patent Number: 5,888,967
[45] Date of Patent: Mar. 30, 1999

[54] USE OF PLASMINOGEN ACTIVATORS TO STIMULATE LOCAL BONE GROWTH

[75] Inventors: Konrad Honold, Penzberg; Lothar Kling, Mannheim; Kurt Lang, Penzberg; Ulrike Leser, München, all of Germany

[73] Assignee: Boehringer Mannheim GmbH, Mannheim, Germany

[21] Appl. No.: 492

[22] PCT Filed: Jul. 30, 1996

[86] PCT No.: PCT/EP96/03345

§ 371 Date: Feb. 9, 1998

§ 102(e) Date: Feb. 9, 1998

[87] PCT Pub. No.: WO97/05891

PCT Pub. Date: Feb. 20, 1997

[30] Foreign Application Priority Data

Aug. 9, 1995 [DE] Germany .................. 19529223.5

[51] Int. Cl.⁶ .................... A61K 38/16; A61K 38/00
[52] U.S. Cl. .................... 514/7; 514/12
[58] Field of Search ........................... 514/7, 12

[56] References Cited

U.S. PATENT DOCUMENTS 5,290,692  3/1994  Suzuki et al. ................ 435/176
5,422,340  6/1995  Dammann et al. ............ 514/12
5,491,082  2/1996  Suzuki et al. ................ 435/176

FOREIGN PATENT DOCUMENTS 0 227 400  12/1986  European Pat. Off. .
0 318 801  11/1988  European Pat. Off. .
0 297 860   1/1989  European Pat. Off. .
0 261 599   9/1997  European Pat. Off. .

OTHER PUBLICATIONS

Database Biosis, 84:252958, Hajduk et al., "The Effect of Streptase Traskolan and Sefril on the Development of Experimental Osteitis 2 . . ." (1981).

Database Medline, 82105103, Hajduk et al., "Effect on Streptokinase, Traskolan and Sefril on the Development of Experimental Osteomyelitis . . ." (1981).

International Publication No. WO 94/07537 published Apr. 14, 1994.

International Publication No. WO 94/15653 published Jul. 21, 1994.

*Primary Examiner*—Theodore J. Criares
*Attorney, Agent, or Firm*—Nikaido Marmelstein Murray & Oram LLP

[57] ABSTRACT

Described herein is a method of promoting osteogenesis in a patient in need thereof by administering a plasminogen activator which activates the zymogen plasminogen by cleavage between arginine 506 and valine 561 to form the serine protease plasmin.

7 Claims, 2 Drawing Sheets

USE OF PLASMINOGEN ACTIVATORS TO STIMULATE LOCAL BONE GROWTH

This application is a 371 of PCT/EP96/03345 filed Jul. 30, 1996.

The invention concerns the use of plasminogen activators to prepare drugs for the local formation of bone as well as pharmaceutical compositions that are suitable for this application. The local formation of bone mass is for example necessary for the healing of bone fractures, in the case of bone destruction caused by tumours, for cosmetic surgery, for the implantation of materials for dental prostheses or for bone replacement materials such as artificial hips or knee joints or to support the incorporation of auxiliary materials such as nails and screws.

It is known that growth factors such as transforming growth factory-β (TGF-β), basic fibroblast growth factor (bFGF) and platelet derived growth factor (PDGF) can positively influence osteogenesis (Pierce et al., J. Cell. Biol. 109 (1989) 429–440).

The object of the invention is to provide further agents which when applied locally support bone growth and bone healing (osteogenesis).

The invention concerns the use of plasminogen activators to produce a drug for local osteogenesis. The plasminogen activator is preferably administered locally at the site in the body to be treated as a solution (injection or infusion) or in a carrier-bound form.

A plasminogen activator is understood as a protein enzyme which activates the zymogen plasminogen by cleavage between arginine 506 and valine 561 to form the serine protease plasmin. Plasmin can cleave numerous proteins including fibrin. Plasminogen activators are for example urokinase (uPA), tissue plasminogen activator (t-PA) and streptokinase. Urokinase is composed of 411 amino acids which can be divided into three domains (epidermal growth factor like domain (EGF), kringle domain and serine protease domain). Urokinase was already purified and characterized in 1982. The recombinant production has been described by Holz, W. E. et al., Biotechnology 3 (1985) 923–929.

t-PA is a protein which is composed of 527 amino acids. It also contains various domains which are referred to as the finger region, EGF-like domain, 2 kringle region and serine protease region. t-PA was purified and characterized by Collen, D. et al., Thromb. Haemostas. 43 (1980) 77–89. The recombinant production is described in Pennica, D. et al., Nature 301 (1983) 214–220. Derivatives and muteins of urokinase and t-PA are described by Harris T. J. R., Protein Engineering 1 (1987) 449–458.

Plasminogen activators are preferably used which have similar properties to human t-PA in particular with regard to plasminogenolytic and immunological properties and with regard to fibrin binding.

Plasminogen activators are particularly preferably used which have a low fibrin binding. Such plasminogen activators are described for example in WO 90/09437 and are preferably composed of the kringle 2 and the protease domain of t-PA.

The application of the plasminogen activator to the site in the body to be treated, preferably bones, can either be achieved in solution and expediently by infusion or injection (preferably local injection) or bound to a carrier. Carrier-bound plasminogen activators can for example be applied to implants as gels, pastes or as a coating.

Biocompatible and preferably biodegradable materials are used as carriers. Preferably the materials themselves also additionally induce wound healing or osteogenesis.

For the application it is preferable to embed the plasminogen activator in polymeric gels or films, to immobilize it in this manner and to apply this preparation directly onto the site on the bones to be treated. Such polymeric base gels or films are for example composed essentially of glycerol, methyl cellulose, hyaluronic acid, polyethylene oxides and/or polyoxamers. Collagen, gelatin and alginate are also suitable and are described for example in WO 93/00050 and WO 93/20859. Other polymers are polylactic acid (PLA) and copolymers of lactic acid and glycolic acid (PLPG) (Hollinger et al., J. Biomed. Mater. Res. 17 (1983) 71–82) as well as the bone derivative "Demineralized Bone Matrix" (DBM) (Guterman et al., Collagen Rel. Res. 8 (1988) 419–431). Polymers are also suitable which are used for example to adsorb TGF-β and are described in EP-A 0 616 814 and EP-A 0 567 391 and synthetic bone matrices according to WO 91/18558.

Materials are also suitable as a carrier for the plasminogen activator that are usually used in the implantation of bone replacement materials or of other therapeutically active substances. Such carriers are for example also based on calcium sulphate, tricalcium phosphate, hydroxyapatite and polyanhydrides. Apart from these biodegradable carriers, carriers are also suitable which are not biodegradable but biocompatible. Such carriers are for example sintered hydroxyapatite, bioglass, aluminates or other ceramic materials (e.g. calcium aluminate phosphate). These materials are preferably used in combination with the biodegradable materials such as in particular polylactic acid, hydroxyapatite, collagen or tricalcium phosphate. Further non-degradable polymers are for example described in the U.S. Pat. No. 4,164,560.

It is particularly preferable to release the plasminogen activator continuously in a small dose at the site of action. Carrier-bound plasminogen activator is preferably used for this. Slow-release pellets from Innovative Research of America, Toledo, Ohio, USA are particularly suitable for this. Pellets are particularly preferably used which release the plasminogen activator over several days preferably up to 100 days at a daily dose of 1–10 mg/kg per day.

The dose of the plasminogen activators for the application purpose according to the invention is expediently between 0.1 μg/ml and 100 μg/ml for administration in solution. The amount of administered solution mainly depends on the size of the bone site to be treated. However, 1 ml per injection is usually administered. The number of administrations is dependent on the prognosis and can be determined by any person skilled in the art.

For an administration in solution the plasminogen activators can be dissolved in water, polyethylene glycol, propylene glycol, ethanol, natural oils such as vegetable oils, benzyl alcohol, sodium chloride and/or various buffers. Other adjuvants that are known to a person skilled in the art can also be used.

The invention is further elucidated by the following examples and figures. The examples are to be understood as aids for carrying out the invention which can be varied within the scope of the teaching of the invention.

EXAMPLE 1

Preparation of Immobilized Plasminogen Activator

Figure 1A:
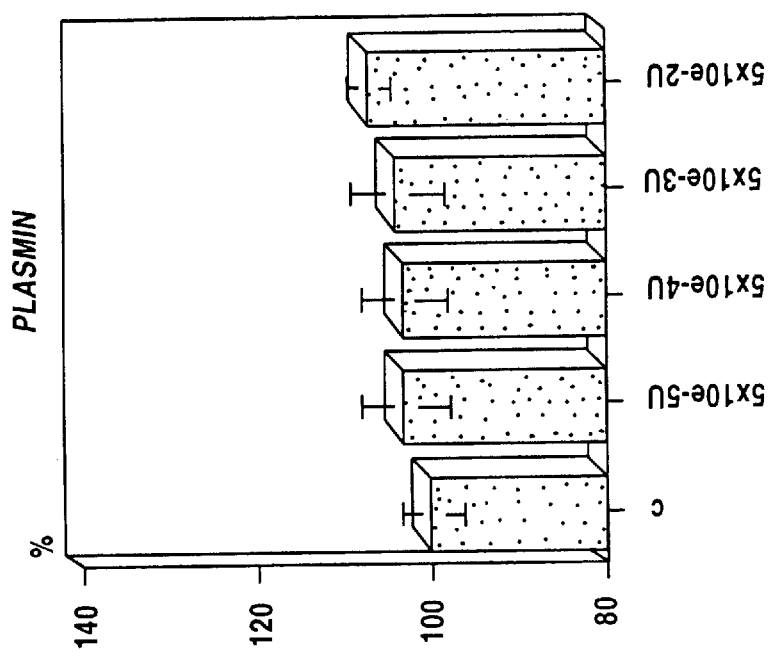
FIG. 1A shows the influence of r-PA (t-PA derivative from kringle 2 and protease) on the bone density (c=control solution (100%)).
Figure 1B:
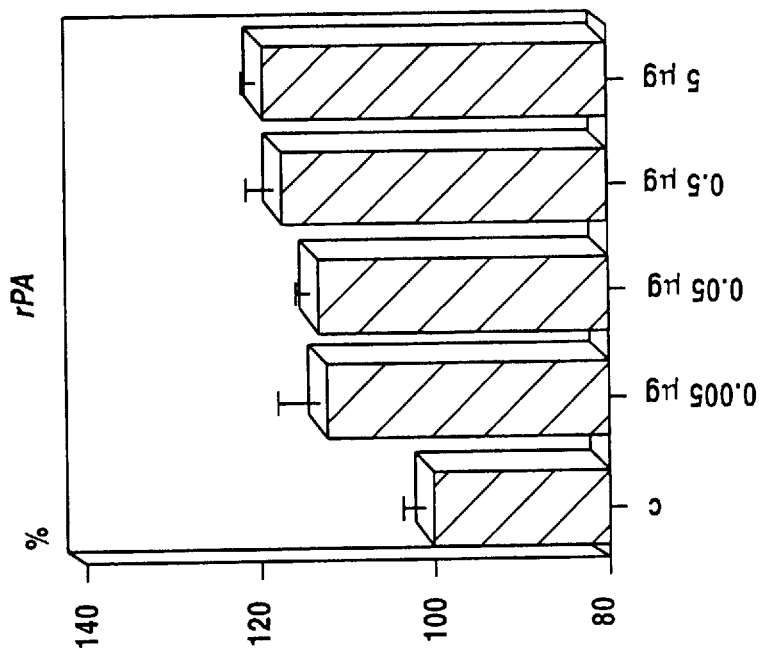
FIG. 1B shows the influence of plasmin on the bone density (c=control solution) (100%)).

TCP (tricalcium phosphate, particle size 150–250 μm, prepared according to WO 94/15653) is pretreated with 0.5 mol/l NaOH for the depyrogenization. The coating with plasminogen activator is carried out by incubating the particles with a solution of 1–1000 mg/l plasminogen activator in 50 mmol/l arginine/HCl, pH 7–7.4.

The adsorption of the plasminogen activator to the ceramic particles was determined by measuring the UV absorbance of the solution before and after incubation with the particles and is ca. 1.5 μg plasminogen activator/mg ceramic particles.

The coated ceramics were washed with water and PBS for 30 minutes in each case. The coating was examined by incubating the washed ceramics with a solution of 0.4 mol/l sodium phosphate buffer, pH 6–8. Plasminogen activator that is eluted from the carrier can be detected in the supernatant. It is also possible to detect the enzymatic/proteolytic activity of the immobilized plasminogen activator.

2. Bone Formation in vivo by Plasminogen Activator

The detection of bone formation is carried out in an experimental model according to Mackie and Trechsel, Bone 11 (1990) 295–300.

2.1 Treatment of the Animals 2.1.1 Plasmin and r-PA

Female, 7 week-old mature Balb/C mice (weight ca. 20 g) were arbitrarily divided into groups of 6 animals each. Various doses of plasmin or plasminogen activator r-PA (recombinant derivative of t-PA (tissue plasminogen activator) from the K2 and P domains, prepared according to WO 90/09437) were administered to four groups, one group served as a control and received the solution buffer without plasminogen activator containing bovine serum albumin (BSA) as a neutral protein. 50 μl of the corresponding solution was administered once daily to each animal directly under the scalp onto the calvaria by means of a Hamilton syringe. The duration of administration was 2×5 days with a two day break between the two application periods.

Solutions of plasmin in PBS were used which contained 1 mg/ml bovine serum albumin (BSA) at concentrations of 0.001 U/ml, 0.01 U/ml, 0.1 U/ml and 1 U/ml or r-PA in PBS/1 mg/ml BSA at concentrations of 0.1 mg/l, 1 mg/l, 10 mg/l and 100 mg/l. Aliquots were stored at −20° C. and each was thawed immediately before administration. In the case of plasmin the daily doses were $5 \times 10^{-5}$ U, $5 \times 10^{-4}$ U, $5 \times 10^{-3}$ U and $5 \times 10^{-2}$ U per animal, in the case of r-PA 0.005 μg, 0.05 μg, 0.5 μg and 5 μg per animal. The calvaria were collected on the 26th day of the experiment (=14th day after the last administration).

2.1.2 r-PA and t-PA t-PA (human tissue plasminogen activator) was prepared recombinantly in CHO cells according to EP-B 0 093 619. t-PA and r-PA were administered as described in 2.1.1. 5 μg/animal (100 mg/l) were used in each case as the dose. 150 mmol/l phosphate buffer, pH 6.0, 10 mmol/l tranexamic acid, 7 mg/ml sucrose, 0.01% Tween®80 was used as the control solution. The duration of administration was 4×5 days with a two day break between the administration periods. The calvaria were collected on the 40th day of the experiment (=14th day after the last administration).

2.1.3 Protease Domain of t-PA

The protease domain was prepared recombinantly in *E. coli* cells according to WO 96/17928. The administration was as described in 2.1.1. 1.15 μg/animal (23 mg/l) or 3.80 μg/animal (76 mg/l) were used in each case as the dose. The control solution used was identical to that described in section 2.1.2. The duration of administration was 4×5 days with a two day break between the administration periods. The calvariae were collected on the 40th day of the experiment (=14th day after the last administration).

2.2 Tissue Preparation

The animals were sacrificed by dislocation of the cervical vertebra and the calvariae were dissected out. A trapezoid piece which essentially consists of the right and left parietal bone and frontal bone was punched out of each calvaria. The punched pieces were fixed for 24 hours at 4° C. in 50% ethanol+1% $CaCl_2$ and subsequently transferred into 70% ethanol for storage.

2.3 X-ray Analysis

The calvarial pieces were removed from the ethanol solution and dried in the air for 30 minutes.

A common X-ray picture was taken of all calvarial pieces (X-ray plate: Structurix D4pDW, 13×18 cm/100, AGFA-GAEVERT Co. X-ray apparatus: Torrex 120, EG&E Co. Astrophysics Research Corporation, 35 kV, 5 mA, 40 sec.). Subsequently the X-ray density (grey value of the calvariae with the aid of a true colour analyser; CBA 800, Wild-Leitz Co.) was quantified in a certain measuring window that was always constant. The measuring window covered the major part of a calvarial half (as a rule the right half) and the sutures were not in the measuring area. The measured values for each dose group were averaged and related to the control (=100%).

2.4 Results

Figure 2:
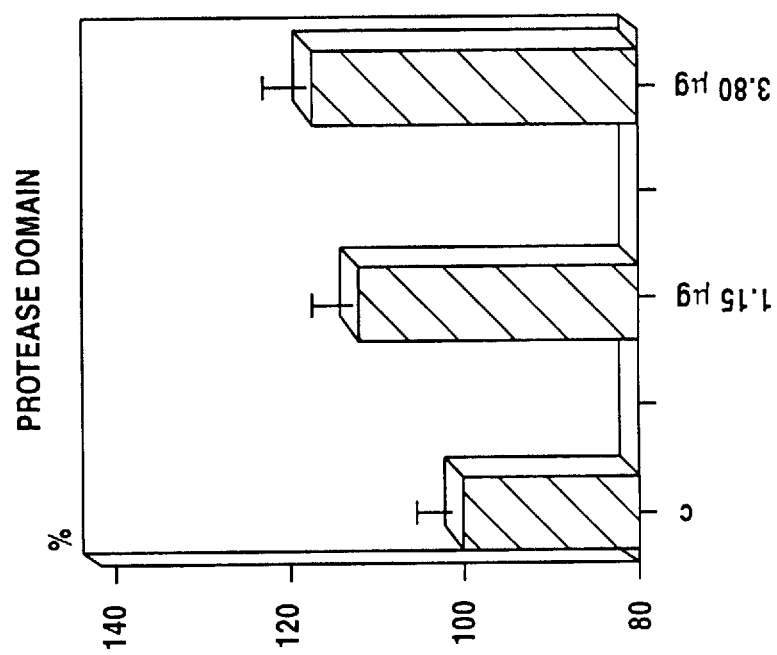
FIG. 2 shows the influence of r-PA and t-PA on the bone density (c=control solution (100%)).
Figure 3:
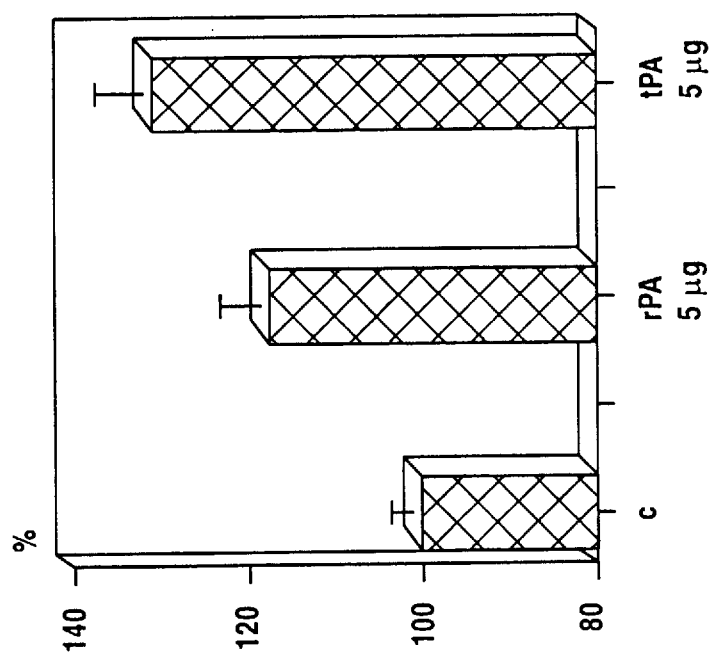
FIG. 3 shows the influence of the protease domain of t-PA on the bone density (c=control solution (100%)).

FIGS. 1A+1B showed the results of the X-ray analysis from 2.1.1. This shows that plasmin has practically no influence on the bone density whereas the plasminogen activator r-PA considerably increases the bone density. FIG. 2 shows the results from example 2.1.2. This shows that r-PA as well as t-PA considerably increases the bone density. FIG. 3 shows the result from example 2.1.3. This shows that the protease domain of t-PA also considerably increases bone density.

List of references

Collen, D. et al., Thromb. Haemostas. 43 (1980) 77–89
EP-A 0 567 391
EP-A 0 616 814
Guterman et al., Kollagen Rel. Res. 8 (1988) 419–431
Harris T. J. R., Protein Engineering 1 (1987) 449–458
Hollinger et al., J. Biomed. Mater. Res. 17 (1983) 71–82
Holz, W. E. et al., Biotechnology 3 (1985) 923–929
Mackie and Trechsel, Bone 11 (1990) 295–300
Pennica, D. et al., Nature 301 (1983) 214–220
Pierce et al., J. Cell. Biol. 109 (1989) 429–440
U.S. Pat. No. 4,164,560
WO 90/09437
WO 91/18558
WO 93/00050
WO 93/20859
WO 94/15653
WO 96/17928

We claim:

1. A method of promoting osteogenesis in a patient in need thereof, comprising administering to the patient an osteogenesis-promoting-effective amount of a plasminogen activator selected from the group consisting of urokinase, tissue plasminogen activator and streptokinase, or a derivative mutein thereof which activates the zymogen plasminogen by cleavage between arginine 506 and valine 561 to form the seine protease plasmin.

2. The method of claim 1, wherein the plasminogen activator is administered via injection directly to a bone site to be treated.

3. The method of claim 1, wherein the plasminogen activator is administered in solution via injection or infusion.

4. The method of claim 3, wherein the solution comprises 0.1 µg/ml to 100 µg/ml of the plasminogen activator.

5. The method of claim 1, wherein the plasminogen activator is applied to a carrier which comprises a bone replacement material, and the carrier is implanted into the patient.

6. The method of claim 1, wherein the plasminogen activator is mixed with a polymeric gel or film, and the gel or film is thereafter applied directly onto a bone site to be treated.

7. The method of claim 1, wherein the plasminogen activator is continuously administered for a period of up to 100 days at a daily dose of 1–10 mg/kg patient.

* * * * *